United States Patent [19]

Laufer

[11] Patent Number: 5,161,481
[45] Date of Patent: Nov. 10, 1992

[54] METHOD FOR INCREASING CRUSTACEAN LARVAL PRODUCTION

[76] Inventor: Hans Laufer, 49 Constance Dr., Manchester, Conn. 06040

[21] Appl. No.: 791,364

[22] Filed: Nov. 14, 1991

[51] Int. Cl.$^5$ ............................................. A01K 61/00
[52] U.S. Cl. ........................................ 119/2; 426/2; 426/805
[58] Field of Search ........................... 119/2, 3, 4, 174; 426/1, 2, 805, 643

[56] References Cited

U.S. PATENT DOCUMENTS

| | | | |
|---|---|---|---|
| 3,830,937 | 8/1974 | Shigeno et al. | 119/2 |
| 4,078,521 | 3/1978 | Laubier | 119/2 |
| 4,239,782 | 12/1980 | Cinquemani | 426/2 |
| 5,076,208 | 12/1991 | Zohar et al. | 119/3 |

FOREIGN PATENT DOCUMENTS

| | | | |
|---|---|---|---|
| 0092297 | 8/1978 | Japan | 119/2 |
| 0097295 | 8/1979 | Japan | 119/2 |
| 0097300 | 8/1979 | Japan | 119/2 |
| 0071358 | 5/1982 | Japan | 119/2 |

OTHER PUBLICATIONS

Payen and Costlow, *Biol. Bull.* 152:199–208 (1977).
Templeton and Laufer, *Int. J. Invert. Reprod.* 6:99–110 (1983).
Vogel and Borst, *Am. Zool.* 29:49A (1989).
Paulus, Ph.D. diss., University of Connecticut, Storrs, (1984).
Laufer et al., *Science* 235: 202–205 (1987).
Laufer et al., *Insect Biochem.* 17:1129–1131.
*Morphogenetic Hormones of Anthropods*, pp. 37–60 (1990).
Borst et al., *Insect Biochem.* 17: 1123–1127 (1987).
Landau et al., *Inverteb. Reprod. and Develop.* 16:165–169 (1989).
Doctoral Thesis of G. Chamberlain, Texas A & M (1986).
Middleditch et al., *J. Chromatog.* 195:359–368 (1980).
Lytle and Lytle, *J. World Aquacult. Soc.* 21:314 (1990).
Lytle et al., *Aquaculture* 89:387–299 (1990).
Laufer and Homola, *NOAA Technical Report NMFS* 106:89–98.
Charmantier et al., *Gen. and Compar. Endocrin.* 70:319–333 (1988).
Costlow, in *Physiological Responses of Marine Biota to Pollutants*, Calabrese et al, eds.:439–457, Academic Press, N.Y. (1977).
Gomez et al. *Science* 179:813–814 (1973).
Hertz and Chang, *Int. J. Invert. Reprod. and Devel.* 10:71–77 (1986).
Hinsch, *Int. J. Invert. Reprod.* 3:237–244 (1981).

*Primary Examiner*—Robert P. Swiatek
*Assistant Examiner*—Todd E. Manahan
*Attorney, Agent, or Firm*—Hamilton, Brook, Smith & Reynolds

[57] ABSTRACT

The disclosure relates to methods and compositions for use in crustacean aquaculture. In one embodiment, a compound having juvenile hormone activity is administered to female crustacea, as a supplement to conventional aquaculture diet, in an amount effective to stimulate an increase in viable larvae production. In a second embodiment, juvenile hormone, in an edible carrier, is supplied as a substitute for annelid worms in a conventional aquaculture diet.

16 Claims, No Drawings

METHOD FOR INCREASING CRUSTACEAN LARVAL PRODUCTION

GOVERNMENT SUPPORT

Work described herein was funded by Grants NA-90AA-D-SG443 and NA-85AA-D-SG101 from the National Sea Grant College program, National Ocean and Atmospheric Administration, U.S. Department of Commerce.

BACKGROUND OF THE INVENTION

In several Asian nations, decapod crustacea (particularly shrimp) have been raised in aquaculture environments for over 2,000 years. Motivation to improve on the antiquated aquaculture technology was provided as a result of a surge in shrimp market demand in the mid-1970s. Taiwan was at the leading edge of the innovation and by 1987 emerged as the world's leading shrimp exporter, surpassing even the fishing nations of Mexico and India.

The egg production of crustaceans (e.g., the white shrimp *Penaeus vannamei*) in aquaculture is currently stimulated by unilateral eye stalk ablation. This enhances egg production and egg laying in some species, whereas others respond inconsistently. In addition to the eyestalk ablation, other factors such as diet, light, temperature and water conditions are carefully controlled to optimize production.

The effects of eyestalk ablation vary with the season of the year and the stage in the molt cycle. Shrimp which are ablated as they prepare to enter their reproductive peak are more conditioned to yield a reproductive (as opposed to a molting) response than those entering a reproductively dormant period.

The fecundity and viability of spawns from ablated females have been reported to be inferior to spawns from females matured in the wild. Furthermore, in comparison to normal mature ovaries, the ovaries from ablated females have been found to be smaller, with a higher lipid composition, and more variable in distribution of yolk among oocytes. These differences presumably are consequences of hormonal insensitivity of ablated shrimp to physiological or environmental conditions such as oocyte differentiation, nutrient storage, food supply or temperature.

An alternative method for increasing the larval production of female crustacea would be of great value to the industry.

SUMMARY OF THE INVENTION

The subject invention relates to compositions and methods for increasing the production of viable larvae by female crustaceans. An effective amount of a juvenile hormone (e.g. methyl farnesoate) is administered to the female crustacean as a supplement to the conventional aquaculture diet which includes annelid worms. A preferred method of administration is oral. A preferred composition for oral administration is a fish meal based crustacean food containing an effective amount of juvenile hormone. Average egg production can be doubled relative to average production by eyestalk ablated females by administering juvenile hormone, as a supplement to the conventional aquaculture diet, as described herein.

In another aspect, the invention relates to an improvement in crustacean aquaculture methods in which annelid worms are omitted from the diet. In the improved method, the shrimp fed experimental diet, without annelid worms, were found to produce a comparable number of larvae when compared with a control population fed in a conventional manner. The cost of the experimental diet is greatly reduced when compared with the conventional diet including annelid worms.

DETAILED DESCRIPTION OF THE INVENTION

An increase in crustacean larval production can result from effects at at least three stages in the reproductive process. For example an increase in larval production can result from increased egg production, increased egg fertility, and/or increased survival rate of fertile eggs to hatching. The desired end result is an increase in the average number of living larvae produced by a female crustacean.

The present invention relates, in one aspect, to an increase in larval production induced by supplementing the conventional aquaculture diet with an effective amount of juvenile hormone. This method improves larval production by favorably affecting reproduction at each of the three stages mentioned above. The invention relates, in a second aspect, to a method for increasing egg fertility and hatchability by substituting, for an expensive component of the conventional aquaculture diet, an inexpensive food comprising juvenile hormone in an edible carrier.

Juvenile hormones are a family of sesquiterpenoid compounds that regulate both metamorphosis and gametogenesis in insects. The genus comprising juvenile hormone, as used herein, includes any compound which, when applied to an insect cuticle, prevents that portion of the cuticle to which it was applied from developing from pupa to adult. Many such compounds are known to those skilled in the art. In fact, the number of such compounds known probably exceeds 100 and many more could be discovered by a simple assay in which a solution containing a compound to be tested is applied to the cuticle of an insect and its effect on development observed. Such an assay is particularly sensitive when the cuticle is punctured prior to hormone application. The hormone can be applied in a wax mixture which is used to seal the puncture.

A partial list of members of the juvenile hormone genus includes methyl farnesoate; farnesoic acid; juvenile hormone I; juvenile hormone II; juvenile hormone III; 8, 11, 14 Eicosatrienoic acid; methoprene and hydroprene (Zoecon Corporation); pyriproxyfen (Sumitomo Corporation) and fenoxycarb (Hoffman LaRoche Corporation). Several of the above-identified compounds are commercially available. The chemical structure of the compounds methoprene; pyriproxyfen and fenoxycarb are set forth below.

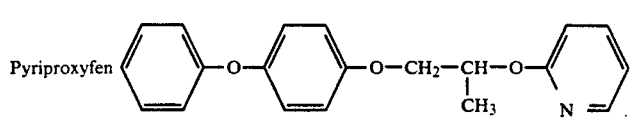

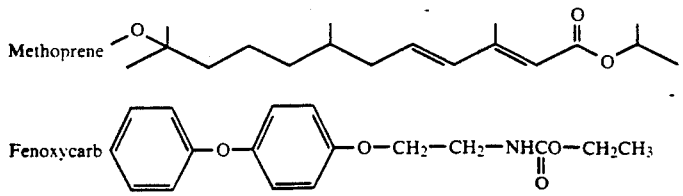

Such compounds, when administered to female crustacea in effective amounts, as a supplement to the conventional aquaculture diet, induce a dramatic increase in larval production. The conventional aquaculture diet includes annelid worms.

The hormone can be administered in a variety of ways. Preferred methods of administration include oral, topical, injection or timed release implantation. Oral administration is best accomplished by formulating the hormone in a crustacean food. Although the hormone can be applied to any food that will be eaten by the curstacean, a preferred formulation method is to supplement a commercially available fish meal based food with the hormone. The commercially available product is produced by mixing ground fish meal with oils and a solidifying agent in a food mixer. The mixed composition is then extruded, typically in a spaghetti form, dried and broken into pellets. Juvenile hormone can be added to any crustacean food as a means for oral administration.

Juvenile hormone can be blended with, or added to, the fish meal-based product at a concentration which is effective in stimulating the increased larval production in female crustacea. This concentration can vary within a wide range. The critical value is the amount of hormone actually ingested by individual female crustaceans. As is shown in the exemplification below, when shrimp are fed experimental diet once per day, as a supplement to the conventional aquaculture diet, the optimal value for the amount of hormone consumed per individual is about 1–4 micrograms per day.

This calculation of the optimum is arrived at by first making certain reasonable assumptions. For example, it is assumed that all of the pellets which are fed to the crustacea are actually eaten by the crustacea. This is verifiable by visual observation. It is further assumed that individual crustacea eat approximately the same amount of hormone containing pellets.

Thus, the lower end of the concentration spectrum is limited by the appetite of the crustaceans. For example, to supply individual crustacea with optimal hormone levels by supplying food which contains the hormone at a very low hormone concentration, it may be necessary to add to the aquaculture tank a quantity of pellets which will exceed the amount which can be consumed by the crustaceans. In this case, although the desired quantity of hormone is added to the aquaculture tank, the amount consumed, on average, by individual females is suboptimal because not all of the pellets are consumed.

The upper end of the concentration spectrum is influenced by the desire to distribute hormone equally among the crustacea in the tank. It would be possible, for example, to formulate a food composition containing the optimum daily concentration of hormone for 100 animals in 100 pellets. However, if pellets were not distributed evenly throughout the tank, or if there was significant disparity in the feeding activity of individual crustacea, the distribution of hormone would be skewed across the population.

By formulating the mixture so that the optimum daily dose per crustacea is contained within a multiplicity of pellets (e.g., 5–20 pellets per animal), the problems referred to above are minimized. As demonstrated in the Exemplification which follows, it has been determined that an effective concentration of juvenile hormone, when administered once daily, falls within the range of about 0.00026% to about 0.0011% by weight in a fish meal based crustacean food composition.

To produce such a composition, the hormone is mixed with fish meal at the appropriate weight ratios and formed so that the hormone remains concentrated when added to an aquaculture environment. Preferably, oils and a solidifying agent are added to the mixture which is subsequently extruded. One reason that this formulation is preferred is because such pellets are not readily soluble in the aquaculture environment. Therefore, the hormone remains concentrated thereby facilitating the administration of an effective dose to individual animals. In a preferred composition, the hormone methyl farnesoate is included at a concentration of about 0.00055% by weight.

Topical administration is most effectively accomplished by dipping female crustacea in a relatively concentrated solution of the desired juvenile hormone. The appropriate concentration of the solution is determined empirically in a manner similar to the methods outlined below for assessing the effectiveness of oral administration. In initial studies a dilution series would be carried out to bracket the preferred range. This initial study would be followed by a topical series designed to more accurately determine the optimum concentration. Topical administration can also be accomplished, albeit less efficiently, by solubilizing juvenile hormone in the aquaculture water. Again, routine experimentation is used to determine preferred concentration ranges.

Injection is also an efficient way to administer hormone to female crustacea. Hormone is solubilized in a buffered solution which is physiologically acceptable to the animal. An initial dilution series beginning at about 0.5 micrograms and increasing to about 10 micrograms of hormone per animal per day would be administered to define the preferred range. An alternative to injection is timed release implant.

In a second aspect, the subject invention relates to the substitution of juvenile hormone, in an edible carrier, for annelid worms in a conventional aquaculture diet. The annelid worms are an expensive component of the conventional aquaculture diet, and the ability to substitute the juvenile hormone in an edible carrier offers a substantial commercial advantage.

EXEMPLIFICATION

Three experiments were conducted in which juvenile hormone was administered to shrimp. The growth conditions common to these experiments, and the method for preparing the experimental feed, is described below.

Growth Conditions

The shrimp used in the studies described herein were *Penaeus vannamei*. The shrimp were cultured in commercial tanks having a volume of about 17,500 liters. Approximately 180 shrimp were contained in each tank (about 100 females and 80 males). An artificial daylight schedule was established through the use of combinations of fluorescent lights.

The lighting was varied to simulate dawn, day, midday, late-day, dusk and night. Actual time differs from the phase of the day which was simulated for the shrimp cultures. At 01:00, one pair of 40 watt fluorescent bulbs was turned on over the center of each tank. At 02:00, four additional pairs of 40 Watt fluorescent bulbs, spaced evenly from the center were turned on. Mid-day was simulated by turning on two additional sets of lights with four, 40 Watt bulbs each. To simulate the transition from mid-day to night, the process was reversed. At 11:00 the two sets of four bulbs were turned off. At about 13:45 the four pairs of 40 Watt bulbs were turned off. Finally, at 14:45, the final pair of 40 Watt bulbs was turned off.

According to the conventional aquaculture feeding schedule, the shrimp were fed five times daily. At about 06:00 the shrimp were fed mussels (11.7 g/kg biomass). At 11:00 the experimental group of shrimp were fed about 0.38 g each of the experimental diet which included methyl farnesoate. A control group was fed the same amount of the commercially available shrimp meal which had been manipulated in exactly the same manner as the experimental diet (discussed in greater detail below), except for the addition of methyl farnesoate. At about hour 13:45, the shrimp were fed annelid bloodworms (58.9 g/kg biomass). Preliminary experiments, discussed in Experiment 3, have shown that annelid bloodworms can be omitted from the diet of the shrimp receiving methyl farnesoate without a serious detrimental impact on larval production. At hour 19:00, the shrimp were fed squid (10.1 g/kg biomass). The fifth feeding was at hour 24:00 a squid and mussel mixture which consisted of squid and mussels in a ratio of 5.0 grams of squid to 5.9 grams mussel per kg of biomass.

Experimental Feed Formulation

The pellets which contained juvenile hormone were prepared by grinding commercial pellets and mixing the ground pellets with a formulation including oils, an anti-oxidant, a solidifying agent (algenate) and the hormone methyl farnesoate. The commercial pellets were Rangen Shrimp Maturation Feed Supplement (Rangen, Inc., Buhl, Id.). The pellets were ground in a model 3 Wiley Mill Grinder (single speed) supplied with a fine mesh filter screen.

Three premixes were formulated and selectively combined. Premix one (control oil premix) contained 67 grams safflower oil, 1 ml anti-oxidant (butylated hydroxy toluene (BHT)) and 30 ml 95% ethanol mixed with 606 grams of ground pellets. Premix two (experimental oil premix) was prepared in the same manner as premix one except that the 30 ml ethanol was replaced by 12, 24 or 48 milligrams of methyl farnesoate in 30 ml of 95% ethanol. Premix three (binding premix) contained 45 grams hexa-metaphosphate and 45 grams sodium alginate combined with 585 grams of ground pellets.

The oil premix (either control or experimental) was blended with 3150 grams of ground pellets. The binding premix was then added to the oil premix/ground pellet blend with 1–4 liters water to yield the ready-to-extrude batch.

The combined premixes were extruded through an extruder equipped with a face plate constructed to have 9 holes of ⅛ inch diameter drilled into an aluminum plate. The extruded moist feed was air dried in a forced air oven at 70° C. After an additional 3–4 hours in the oven at room temperature the feed was dry. On moving the feed from the trays to individual plastic bags for each batch the feed breaks naturally into one to two inch pellets. The reformulated pellets were prepared in 4.5 kilogram batches containing 0, 12 mg (1×), 24 mg (2×) and 48 mg (4×) of hormone per batch.

Experiment 1

Two tanks were used in this experiment. Tank 1 animals (control animals) were fed commercial pellets reformulated as described above for the experimental diet except for the addition of a compound having juvenile hormone activity. Tank 1 contained 88 females and approximately 70 males. Of these 88 females, 44 were unablated and 44 had undergone eyestalk ablation.

Tank 2 animals (experimental animals) were fed 1× pellets containing hormone which were prepared as described above. Tank 2 contained 88 females and approximately 70 males. Of these 88, 44 were unablated and 44 had undergone eyestalk ablation.

Each female shrimp was numbered with a tag. Each was inspected daily, at about hour 15:00, for having mated. In such a case, a white spermatophore could be seen on the ventral side. Mated females were isolated into individual spawning tanks. The morning after egg-laying, the number of eggs were estimated in the spawning tank and the eggs were estimated as to fertility by microscopic observation. The percent of fertile eggs in each spawn was recorded. Following incubation of the eggs the number of larval nauplei hatched was estimated for each spawn and a percent hatch was calculated based on the percent fertile eggs.

Table 1 below represents the results of the experiment. The percentage increase reported for the experimental animals is relative to the control animals. In summary, total egg production in the experimental animals showed an increase of 21%. The fertility of eggs produced by the experimental animals increased by 36%. The survival of fertile eggs to hatching increased by 79% in the experimental animals. The average number of larvae produced per batch increased by 50% in the experimental animals.

An interesting observation was that ablated female controls never spawned more than twice during the experimental period which lasted about 40 days. Typically these females spawned only once. Individual females from the experimental group, on the other hand, were observed to spawn up to 4 times in the experimental period.

There were 5 of 44 females that were treated with hormone, but were unablated that spawned compared to 1 of the controls. Here also, two spawned more than once during the experimental period. This result is very significant since these animals were otherwise untreated.

In summary, the results of Experiment 1 demonstrate that the experimental groups, both ablated and unablated compared to the controls produced a statistically higher number (163%) of living larvae than did the controls. Assuming that all of the pellets are consumed, and assuming that each shrimp consumes an equal quantity of pellet, each shrimp in the experiments described above consumed about 0.38 grams of 1× pellets containing about 1.0 micrograms of hormone per day.

TABLE 1

| | Egg and Larva Production | | | |
|---|---|---|---|---|
| | # Spawns | # Eggs | % Fertile | # Larvae | % Hatched |
| Control (Tank 1) | | | | | |
| Ablated | 30 | 6,535,000 | 47 | 2,763,000 | 42 |
| Unablated | 1 | 288,000 | 91 | 208,000 | 81 |
| | | Total Larvae | | 2,971,000 | |
| Experimental (Tank 2) | | | | | |
| Ablated | 28 | 5,825,000 | 70 | 3,850,000 | 66 |
| Unablated | 7 | 1,490,000 | 75 | 990,000 | 66.4 |

| | Total Larvae | 4,840,000 |
|---|---|---|

$$\frac{\text{Exp. Larval Total}}{\text{Cont. Larval Total}} \frac{4,840,000}{2,971,000} \times 100 = 163\%$$

Experiment 2

Experiment 2 involved the use of 5 aquaculture tanks (Tank 3 through Tank 8) of the type described in Experiment 1. Tank 3 (T3) was a control tank which contained 100 females of which 10 were unablated. Tank 4 (T4) was an experimental tank which contained 99 females of which 9 were unablated. The shrimp in Tank 4 were fed pellets containing 12 mg of hormone per 4½ kilogram batch (1×). Tank 5 (T5) was an experimental tank containing 85 females all of which were unablated. The pellets fed to the animals in tank 5 contained 24 mg hormone per 4½ kilogram batch (2×). Tank 6 (T6) was an experimental tank containing 100 females, of which 10 were unablated. The pellets fed to the tank 6 animals were 24 mg hormone per 4½ kilogram batch (2×). Tank 7 (T7) was an experimental tank containing 100 females, 10 of which were unablated. The pellets fed to the tank 7 animals contained 48 mg hormone per 4½ kilogram batch (4×). Each of the tanks contained a number of males, the total number of males being approximately 80% of the female population.

TABLE 2

| | Egg and Larva Production | | | |
|---|---|---|---|---|
| Treatment | | # Eggs | % Fertility | # Larvae | % Hatched |
| T3 Ablated | 0 | 15,534,000 | | 6,916,000 | |

TABLE 2-continued

| | Egg and Larva Production | | | |
|---|---|---|---|---|
| Treatment | | # Eggs | % Fertility | # Larvae | % Hatched |
| T3 Unablated | 0 | 629,000 | | 190,000 | |
| | | 16,163,000 | 44 | 7,106,000 | 81 |
| | avg. | 172,086 | | 73,602 | |
| T4 Ablated | 1× | 18,132,000 | | 7,732,000 | |
| T4 Unablated | 1× | 161,000 | | 105,000 | |
| | | 18,293,000 | 47 | 7,837,000 | 84 |
| | avg. | 182,141 | | 80,545 | |
| T5 Ablated | 2× | — | | — | |
| T5 Unablated | 2× | 3,242,000 | 44 | 1,354,000 | 92 |
| | avg. | 216,133 | | 90,267 | |
| T6 Ablated | 2× | 26,105,000 | | 12,797,000 | |
| T6 Unablated | 2× | 803,000 | | 343,000 | |
| | | 26,908,000 | 51 | 13,140,000 | 85 |
| | avg. | 168,627 | | 82,728 | |
| T7 Ablated | 4× | 25,906,000 | | 10,877,000 | |
| T7 Unablated | 4× | 1,705,000 | | 1,207,000 | |
| | | 27,611,000 | 47 | 12,084,000 | 79 |
| | avg. | 179,091 | | 78,383 | |

TABLE 3

| Female Treatment | # | Multiplicity of Spawns | | | | | | | | |
|---|---|---|---|---|---|---|---|---|---|---|
| | | 1× | 2× | 3× | 4× | 5× | 6× | 7× | 8× | 10× |
| T3 Ablated | 0 | 90 | 25 | 13 | 7 | 4 | | | | |
| T3 Unablated | 0 | 10 | 4 | | | | | | | |
| T4 Ablated | 1× | 90 | 23 | 12 | 8 | 1 | 3 | | 1 | |
| T4 Unablated | 1× | 9 | 1 | | | | | | | |
| T5 Ablated | 2× | 0 | | | | | | | | |
| T5 Unablated | 2× | 85 | 9 | 3 | | | | | | |
| T6 Ablated | 2× | 90 | 17 | 21 | 13 | 7 | 3 | 1 | | 1 |
| T6 Unablated | 2× | 10 | 4 | | | | | | | |
| T7 Ablated | 4× | 90 | 17 | 14 | 13 | 5 | 5 | 1 | | 1 |
| T7 Unablated | 4× | 10 | | 4 | | | | | | |

As shown in Tables 2 and 3, the 2× dose of hormone nearly doubled the production of viable larvae. Specifically, an increase of 184.9% was observed. The 4× dose did not increase the benefit of hormone. In fact, there is a slight decrease in larvae as compared to the 2× dose. Larvae production in the 1× dose was about 110% of the control level.

Hormone treatment has a dramatic effect on the multiplicity of spawns among individual females during the experimental period. In tank 8 (controls) there were 29 single spawns and 24 multiple spawns. No females spawned more than 4 times during the experimental period. While treatment with hormone produced in the 4× dose 17 single spawns and 43 multiple spawning females with one producing 10 spawns.

Experiment 3

Experiment 3 was conducted in two aquaculture tanks (tanks 7 and 8). Tank 7 contained 80 ablated females, 20 non-ablated females and about 80 males. The shrimp in tank 7 were fed the conventional aquaculture diet described above. This diet includes annelid worms, a natural food for the shrimp in the wild.

In tank 8, the number of shrimp was the same as that described in Tank 7. The shrimp in tank 8 were fed 2× experimental diet at 11:00 and squid and mussels were substituted for the annelid worms at 14:00.

As shown in Table 4, preliminary data shows that the average number of spawnings, and the average number of eggs produced per spawn, are reduced significantly in the tank 8 animals which had been fed the 2× experimental diet instead of the annelid worms. The reason for this differential is probably due to the fact that the shrimp prefer the annelid worms and consume them in greater quantity than the experimental pellet diet.

However, the reduction in spawning frequency and egg production per spawn was offset by the beneficial effect of juvenile hormone on the fertility of the eggs produced and the hatchability of the first stage larvae. Fertility increased from 33% to 49% and hatchability was improved from 71% to 83%. This increase in the rates of fertility and hatchability resulted in an average production of about 72,000 nauplei per spawn, as compared to an average of about 55,000 nauplei per spawn in the tank 7 animals. The difference in total nauplei yield in the tank 7 and tank 8 groups was statistically insignificant.

Given the significant difference in the relative cost of the experimental pellets as compared with the annelid worms, the method described offers a substantial commercial advantage.

TABLE 4

| Tank # | Treatment MF | Treatment Worms | # Females Ablated | Un-ablated | # Mated-Spawned | Total # Eggs × 10³ | % Fertile | Total Nauplei × 10³ | % Hatched | Ave. Eggs Per Spawn × 10³ | Ave. Nau. Per Spawn × 10³ |
|---|---|---|---|---|---|---|---|---|---|---|---|
| | Control | | | | | | | | | | |
| 7 | — | + | 80 | | 142 | 22,653 | 32 | 7,089 | 70 | 158 | 50 |
| | | | | 20 | 13 | 3,110 | 48 | 1,499 | 89 | 239 | 115 |
| | Totals | | 100 | | 155 | 25,763 | 33 | 8,588 | 71 | 165 | 55 |
| | Experimental | | | | | | | | | | |
| 8 | 2× | — | 80 | | 112 | 16,279 | 48 | 7,717 | 82 | 145 | 69 |
| | | | | 20 | 4 | 1,051 | 60 | 653 | 96 | 263 | 163 |
| | Totals | | 100 | | 116 | 17,330 | 49 | 8,370 = 98% of control | 83 | 149 | 72 = 131% of control |

Equivalents

Those skilled in the art will know, or be able to ascertain using no more than routine experimentation, many equivalents to the specific embodiments of the invention described herein. These and all other equivalents are intended to be encompassed by the following claims.

I claim:

1. A method for increasing the production of viable larvae by female crustaceans in aquaculture comprising administering an effective amount of a compound having juvenile hormone activity to the crustaceans.

2. A method of claim 1 wherein the crustacean is a decapod.

3. A method of claim 2 wherein the decapod is a shrimp.

4. A method of claim 1 wherein the compound is selected from the group consisting of methyl farnesoate; farnesoic acid; juvenile hormone I; juvenile hormone II; juvenile hormone III; 8, 11, 14 Eicosatrienoic acid; methoprene; hydroprene; fenoxycarb and pyriproxyfen.

5. A method of claim 4 wherein the compound is administered orally.

6. A method of claim 4 wherein the compound is administered topically.

7. A method of claim 4 wherein the compound is administered by injection.

8. A crustacean food comprising a fish meal blend containing a compound having juvenile hormone activity at a concentration of about 0.00026% to about 0.0011% by weight.

9. A crustacean food of claim 8 wherein the compound is selected from the group consisting of methyl farnesoate; farnesoic acid; juvenile hormone I; juvenile hormone II; juvenile hormone III; 8, 11, 14 Eicosatrienoic acid; methoprene; hydroprene; fenoxycarb and pyriproxyfen.

10. An extruded crustacean food comprising a fish meal blend containing methyl farnesoate at a concentration of about 0.00055% by weight.

11. In a method for raising shrimp in aquaculture, the improvement comprising dispensing to the shrimp, once daily, a crustacean food comprising a fish meal blend containing a compound having juvenile hormone activity at a concentration of about 0.00026% to about 0.0011% by weight.

12. A method of claim wherein the compound is selected from the group consisting of methyl farnesoate; farnesoic acid; juvenile hormone I; juvenile hormone II; juvenile hormone III; 8, 11, 14 Eicosatrienoic acid; methoprene; hydroprene; fenoxycarb and pyriproxyfen.

13. A method of claim 11 wherein the compound is methyl farnesoate.

14. A method for increasing the rate of fertility and hatchability of eggs produced by female crustacea in aquaculture comprising reducing the quantity of, or eliminating, annelid worms from the conventional aquaculture diet and substituting therefor an effective amount of a compound having juvenile hormone activity in an edible carrier.

15. A method of claim 14 wherein the compound is selected from the group consisting of methyl farnesoate; farnesoic acid; juvenile hormone I; juvenile hormone II; juvenile hormone III; 8, 11, 14 Eicosatrienoic acid; methoprene; hydroprene; fenoxycarb and pyriproxyfen.

16. A method of claim 14 wherein the edible carrier is an extruded fish meal blend.

* * * * *

UNITED STATES PATENT AND TRADEMARK OFFICE
CERTIFICATE OF CORRECTION

PATENT NO. : 5,161,481

DATED : November 10, 1992

INVENTOR(S) : Hans Laufer

It is certified that error appears in the above-identified patent and that said Letters Patent is hereby corrected as shown below:

Column 10, Claim 12, line 37, after claim insert ---11---.

Signed and Sealed this

Nineteenth Day of October, 1993

Attest:

BRUCE LEHMAN

Attesting Officer    Commissioner of Patents and Trademarks